(12) United States Patent
John

(10) Patent No.: US 11,937,840 B2
(45) Date of Patent: *Mar. 26, 2024

(54) ENDOSCOPIC SUTURE CUTTER

(71) Applicant: UNITED STATES ENDOSCOPY GROUP, INC., Mentor, OH (US)

(72) Inventor: Keith R. John, Chardon, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 425 days.

This patent is subject to a terminal disclaimer.

(21) Appl. No.: 17/164,442

(22) Filed: Feb. 1, 2021

(65) Prior Publication Data

US 2021/0220002 A1 Jul. 22, 2021

Related U.S. Application Data

(63) Continuation of application No. 15/818,030, filed on Nov. 20, 2017, now Pat. No. 10,905,449, which is a (Continued)

(51) Int. Cl.
*A61B 17/29* (2006.01)
*A61B 17/00* (2006.01)
(Continued)

(52) U.S. Cl.
CPC ........ *A61B 17/29* (2013.01); *A61B 17/00234* (2013.01); *A61B 17/0467* (2013.01); *A61B 17/320016* (2013.01); *A61B 2017/00296* (2013.01); *A61B 2017/00438* (2013.01); *A61B 17/0469* (2013.01); *A61B 2017/2905* (2013.01);
(Continued)

(58) Field of Classification Search
CPC .......... A61B 17/00234; A61B 17/0467; A61B 17/0469; A61B 17/29; A61B 17/320016; A61B 17/3201; A61B 17/3205; A61B 2017/00296; A61B 2017/00438; A61B 2017/2905; A61B 2017/2926; A61B 2017/2932; A61B 2017/2939; A61B 2017/320044; A61B 10/06; A61B 2018/146

See application file for complete search history.

(56) References Cited

U.S. PATENT DOCUMENTS 4,763,668 A 8/1988 Macek
5,228,451 A 7/1993 Bales et al.
(Continued)

OTHER PUBLICATIONS

Office Action from U.S. Appl. No. 14/703,846 dated Feb. 1, 2017.
(Continued)

*Primary Examiner* — Robert A Lynch
(74) *Attorney, Agent, or Firm* — Calfee, Halter & Griswold LLP

(57) ABSTRACT

A rotatable jaw device for use with an endoscope, and method for using such a device. The device includes a fork, and two jaws pivotally mounted to the fork. The jaws are movable between a predetermined closed position and a predetermined open position. At least one jaw has at least one protrusion on a surface of the jaw. The at least one protrusion prohibits movement of the two jaws in the opening direction beyond the predetermined open position.

17 Claims, 5 Drawing Sheets

Related U.S. Application Data continuation of application No. 14/703,841, filed on May 4, 2015, now Pat. No. 9,820,767.

(60) Provisional application No. 61/987,961, filed on May 2, 2014.

(51) Int. Cl.
  *A61B 17/04* (2006.01)
  *A61B 17/32* (2006.01)
  *A61B 17/3201* (2006.01)

(52) U.S. Cl.
  CPC ......... *A61B 2017/2926* (2013.01); *A61B 2017/2932* (2013.01); *A61B 2017/2939* (2013.01); *A61B 2017/2947* (2013.01); *A61B 2017/320044* (2013.01); *A61B 17/3201* (2013.01)

(56) References Cited

U.S. PATENT DOCUMENTS

| | | | | |
|---|---|---|---|---|
| 5,282,806 A | * | 2/1994 | Haber | A61B 17/29 606/208 |
| 5,312,434 A | | 5/1994 | Crainrich | |
| 5,366,467 A | * | 11/1994 | Lynch | A61B 17/320016 606/174 |
| 5,486,189 A | | 1/1996 | Mudry | |
| 5,496,347 A | * | 3/1996 | Hashiguchi | A61B 17/29 606/174 |
| 5,569,243 A | * | 10/1996 | Kortenbach | A61B 18/1445 606/174 |
| 5,893,874 A | * | 4/1999 | Bourque | A61B 17/29 606/208 |
| 2003/0069598 A1 | | 4/2003 | Miser | |
| 2005/0043758 A1 | * | 2/2005 | Golden | A61B 10/06 606/205 |
| 2006/0258954 A1 | * | 11/2006 | Timberlake | A61B 10/06 606/205 |
| 2006/0271101 A1 | | 11/2006 | Saadat | |
| 2007/0049966 A1 | | 3/2007 | Bonadio | |
| 2007/0072466 A1 | | 3/2007 | Miyamoto | |
| 2008/0243175 A1 | | 10/2008 | Moore | |
| 2009/0209946 A1 | | 8/2009 | Swayze | |
| 2010/0131005 A1 | | 5/2010 | Conlon | |
| 2016/0066947 A1 | | 3/2016 | Mitelberg et al. | |

OTHER PUBLICATIONS

Amendment from U.S. Appl. No. 14/703,846 dated May 1, 2017.
Office Action from U.S. Appl. No. 14/703,841 dated Mar. 24, 2017.
Amendment from U.S. Appl. No. 14/703,841 dated Jun. 26, 2017.
Notice of Allowance from U.S. Appl. No. 14/703,846 dated May 24, 2017.
Notice of Allowance from U.S. Appl. No. 14/703,841 dated Jul. 18, 2017.
Office Action from U.S. Appl. No. 15/714,381 dated Jun. 24, 2019.
Notice of Allowance from U.S. Appl. No. 15/714,381 dated Feb. 6, 2020.
Corrected Notice of Allowability from U.S. Appl. No. 15/714,381 dated May 14, 2020.
Office Action from U.S. Appl. No. 15/818,030 dated Jul. 23, 2019.
Office Action from U.S. Appl. No. 15/818,030 dated Nov. 5, 2019.
Office Action from U.S. Appl. No. 15/818,030 dated Mar. 9, 2020.
Office Action from U.S. Appl. No. 15/714,381 dated Nov. 22, 2019.
Office Action from U.S. Appl. No. 15/818,030 dated Jun. 22, 2020.
Notice of Allowance from U.S. Appl. No. 15/818,030 dated Oct. 7, 2020.

* cited by examiner

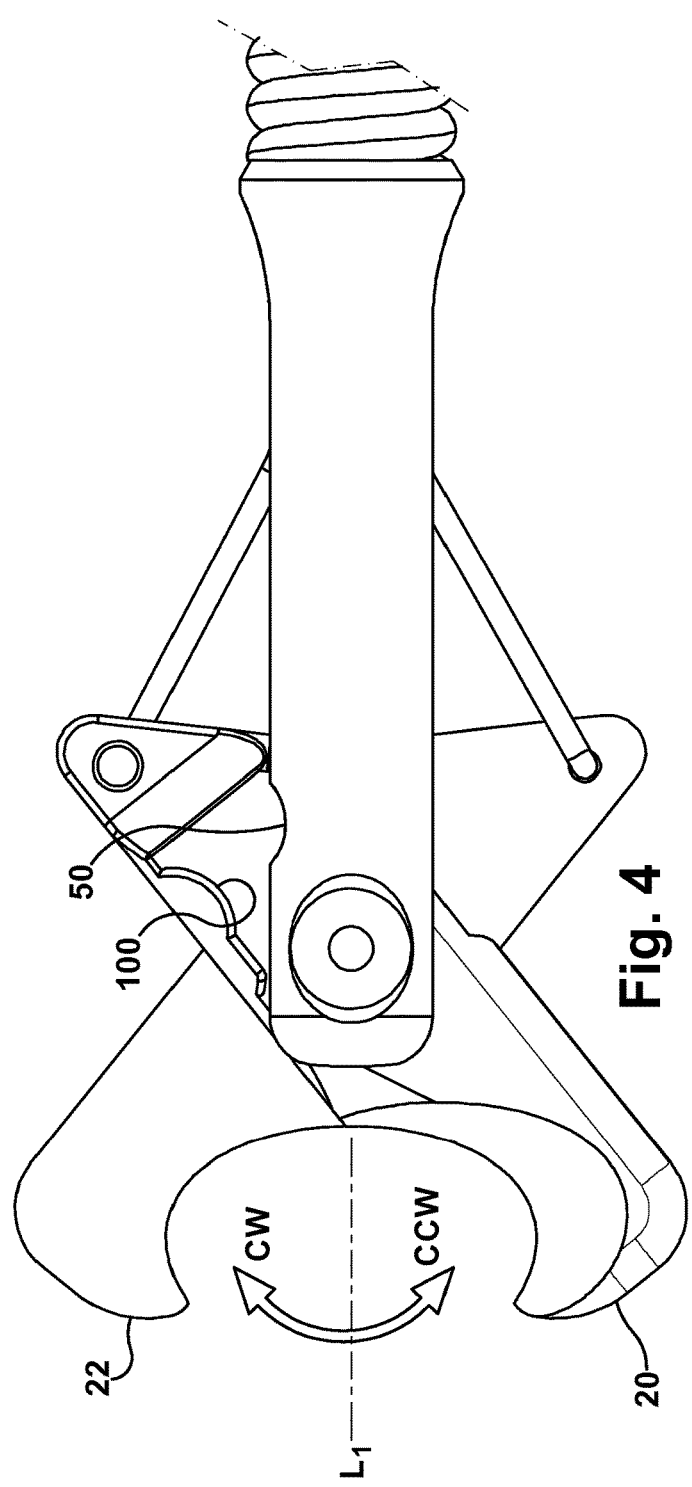
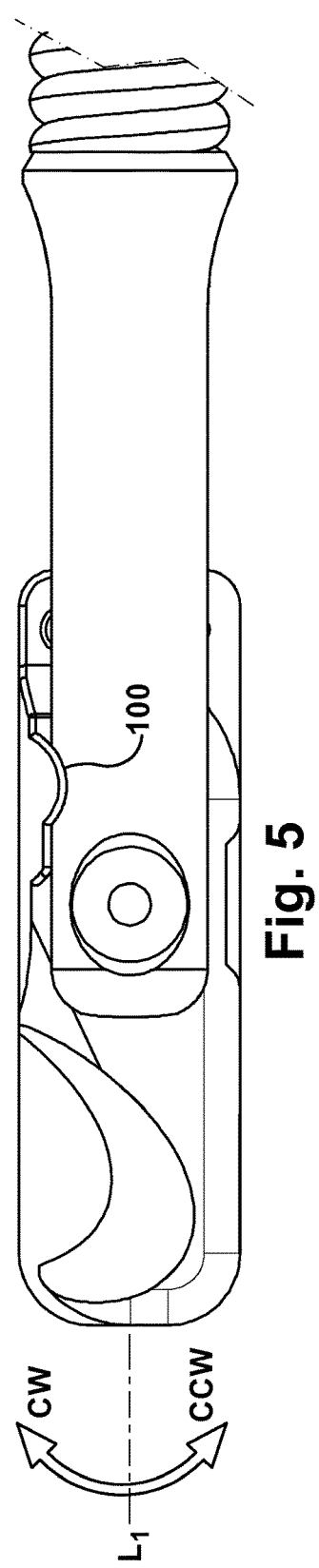

ENDOSCOPIC SUTURE CUTTER

CROSS-REFERENCE TO RELATED APPLICATIONS

This application is a continuation of and claims the benefit of and priority to U.S. patent application Ser. No. 15/818,030, filed Nov. 20, 2017, which is a continuation of U.S. patent application Ser. No. 14/703,841, entitled ENDOSCOPIC SUTURE CUTTER and filed May 4, 2015, now U.S. Pat. No. 9,820,767, issued Nov. 21, 2017, which claims priority to U.S. Provisional Patent Application Ser. No. 61/987,961, entitled ENDOSCOPIC SUTURE CUTTER filed May 2, 2014, the entire disclosures of which are incorporated herein by reference, to the extent that it is not conflicting with the present application.

BACKGROUND

Endoscopes are well-known in the medical arts and are commonly used for numerous medical procedures. One such procedure is removing sutures from the inside of a human subject, such as from the wall of the gastrointestinal tract. One conventional technique for removing sutures is using a cutting tool in an endoscopic procedure.

Known cutting devices in the art have one or two jaws which pivot relative to a base. The jaw may be pivoted by a user operating a handle at a proximal end of the device and at a proximal location outside of the endoscope. Serious complications may arise during suture removal procedures when the jaws of the cutter become stuck, either in an over-closed position or in an over-opened position.

SUMMARY

The present application describes a rotatable jaw device for use with an endoscope.

In an exemplary embodiment, a rotatable jaw includes a fork, and two jaws pivotally mounted to the fork. The jaws are movable between a predetermined closed position and a predetermined open position. The jaws may have one or more protrusions on a jaw surface which may limit rotational movement of the jaws.

Further features and advantages of the invention will become apparent from the following detailed description made with reference to the accompanying drawings.

BRIEF DESCRIPTION OF THE DRAWINGS

Features and advantages of the general inventive concepts will become apparent from the following detailed description made with reference to the accompanying drawings.

FIG. 4 is a front view of the distal end of the endoscopic suture cutter of FIG. 1, with the jaws of the cutter shown in an open position;

FIG. 5 is a front view of the distal end of the endoscopic suture cutter of FIG. 1, with the jaws of the cutter shown in a closed position;

DETAILED DESCRIPTION

Figure 1:
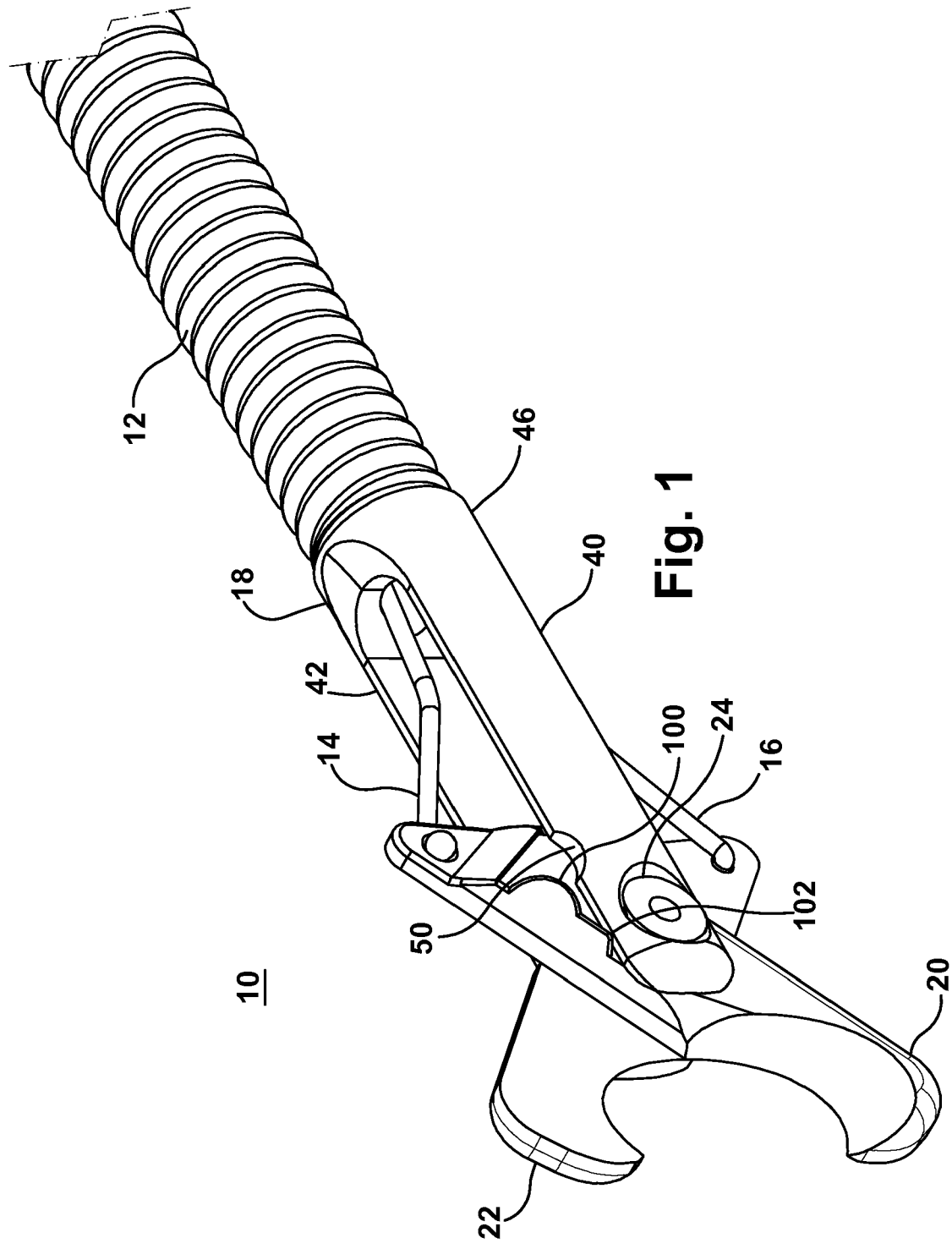
FIG. 1 is a front perspective view of the distal end of an endoscopic suture cutter.

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

In discussing the invention, the terms "proximal" and "distal" are often used. These terms are used to describe a position or a direction with reference to the operator of the tool. For example, the proximal position or proximal direction is toward the user or operator of the tool, and the distal position or direction is away from the user or operator of the tool, i.e., position or direction toward the suture.

After an endoscopic surgical procedure, sutures are often used to secure a wound closed and promote healing. Certain types of sutures, such as absorbable sutures, are left to disintegrate over time and other types of sutures, such as non-absorbable sutures, require removal at a later date. For example, sutures requiring removal include braided sutures made of polypropylene or coated with plastic. To remove a suture in the gastrointestinal tract, the patient may be intubated with an endoscope. After positioning the endoscope inside of the patient and locating the suture to be cut, the user inserts the device into the accessory channel of the endoscope. A conventional cutter has one or two jaws which are operable by a handle having a base and a slider.

Several limitations exist with conventional suture cutters and suture removal techniques. Despite careful use, the slider may be moved too hard or too far in the opening direction, thus causing the jaws of a cutter to be rotated to a so-called "over-opened" position. In other words, the jaws may be rotated beyond a desired open position and become stuck, so that the jaws may not be closed by sliding the handle. The jaws in this position may be locked in a perpendicular, or just past perpendicular, position relative the base. This position is sometimes referred to in the art as the "T-bone" position. When the jaw reach the T-bone position, or any undesired open position and become stuck, the tool can no longer be removed through the channel of the endoscope. This condition may require surgery from outside the body and through the gastrointestinal wall, which severely complicates an otherwise relatively routine endoscopic procedure.

The jaws of a conventional cutter may be rotated to a so-called "over-closed" position. In other words, despite careful use, the slider may be moved too hard or too far in the closing direction, thus causing the jaws of a cutter to be rotated beyond a desired closed position and become stuck, so that the jaws may not be opened by sliding the handle. The jaws in this position may be locked in just past parallel position relative to the base. When the jaw reaches an undesired closed position and become stuck, the tool can no longer be opened and must be removed from the endoscope. This condition may require manual opening of the jaws or more likely a new and sterile cutter will be required. This condition adds time and cost to the procedure.

Various solutions to prevent the over-opened and over-closed condition have been considered in the art. One considered solution uses a bump or stopper on the inside surface of the jaw has been considered. A bump in this location on a jaw would block further opening of the pair of jaws when the bump intersects with the other jaw, and block further closing of the pair of jaws when the bump intersects with the other jaw. However, a bump on the inside surface of the jaw adds complexity to the requirement of sharpening the blade, such as for example, by eliminating any automated side-to-side sharpening of the inside surface.

The present invention is directed to an endoscopic tool which includes two jaws which are each pivotally mounted to a fork. At least one jaw is advantageously shaped to prohibit over-closing beyond a desired position and at least one jaw is advantageously shaped to prohibit over-opening beyond a desired position.

The present invention may be practiced as various types of two device, such as an endoscopic suture cutter that includes a handle, a spring sheath catheter, two control wires, a fork, and two jaws pivotally mounted to the fork. The jaws may be manipulated between a desired open position and a desired closed position. A bump on the outside surface of each jaw prohibits the jaws to be opened beyond the desired open position. Thus, an over-opened condition is prohibited. Another bump on the outside surface of each jaw prohibits the jaws to be closed beyond the desired closed position. Thus, an over-closed condition is prohibited. Neither bump is on the inside surface of the jaw, which advantageously maintains an entirely smooth inner surface.

In an exemplary embodiment of the invention, a rotatable jaw device for use with an endoscope is disclosed. The device includes a fork and two jaws pivotally mounted to the fork. The jaws are movable between a predetermined closed position and a predetermined open position. At least one jaw has at least one protrusion on a surface of the jaw. The at least one protrusion prohibits movement of the two jaws in the opening direction beyond the predetermined open position.

In another exemplary embodiment of the invention, a cutting device for use with an endoscope is disclosed. The cutting device includes a fork, and a first jaw and a second jaw. The first jaw and the second jaw are pivotally mounted to the fork and rotatable between a predetermined closed position and a predetermined open position. Each jaw has at least one protrusion on a surface of the jaw. The at least one protrusion contacts the fork to prohibit movement of the two jaws in the opening direction beyond the predetermined open position.

In another exemplary embodiment of the invention, a cutting device for use with an endoscope is disclosed. The cutting device includes a body, a handle mounted to and movable relative to the body, a catheter having a first end fixed to the body and a second end, the catheter defining a passage and an opening at the second end, a fork having two prongs and attached to the distal end of the conduit, a first jaw and a second jaw, pivotally mounted to the fork within the two prongs, and dependently movable between a predetermined closed position and a predetermined open position, and a first wire attached to a proximal end of the first jaw, and a second wire attached to a proximal end of the second jaw. The jaws are rotatable between the predetermined closed position and the predetermined open position by operation of the handle. A combination of the first jaw and the second jaw have a total of at least two protrusions on a surface of a jaw. At least one protrusion on a surface of a jaw to prohibit movement of the two jaws in the opening direction beyond the predetermined open position and at least one protrusion on a surface of a jaw to prohibit movement of the two jaws in the closing direction beyond the predetermined closed position.

The bump which prohibits an over-opened condition has other benefits. By giving a physician confidence against an over-opened condition, the physician may apply pressure in the opening direction to hold the jaws firmly in the maximum open condition. Thus, one or more of the jaws may be used as a picking or pulling tool to loosen up a bundle of imbedded sutures. Often the sutures are applied in a manner which does not allow or permit a simple cut of a single and distinct suture to allow removal, and picking is necessary to position a suture in a cut-ready position for the physician. With conventional cutting tool, a physician must be very cautious as to not over-open the cutter while trying to forcefully separate a bundle of sutures.

Referring now to the drawings, FIG. 1 is a front perspective view of the distal end of an endoscopic suture cutter 10. The cutter 10 includes a handle, a spring sheath catheter 12, two control wires 14, 16, a fork 18, and two jaws 20, 22 pivotally mounted to the fork 18 by a rivet 24. The control wires 14, 16 run through the sheath toward the proximal end on the cutter 10. Movement of the control wires 14, 16 in the distal direction opens the jaws 20, 22 and movement of the control wires in the proximal direction closes the jaws 20, 22. Movement of the control wires 14, 16 is controlled by manipulation of the handle by a user. The way in which the jaws are secured together, and to the fork, may be modified in the practice of this invention.

Figure 9:
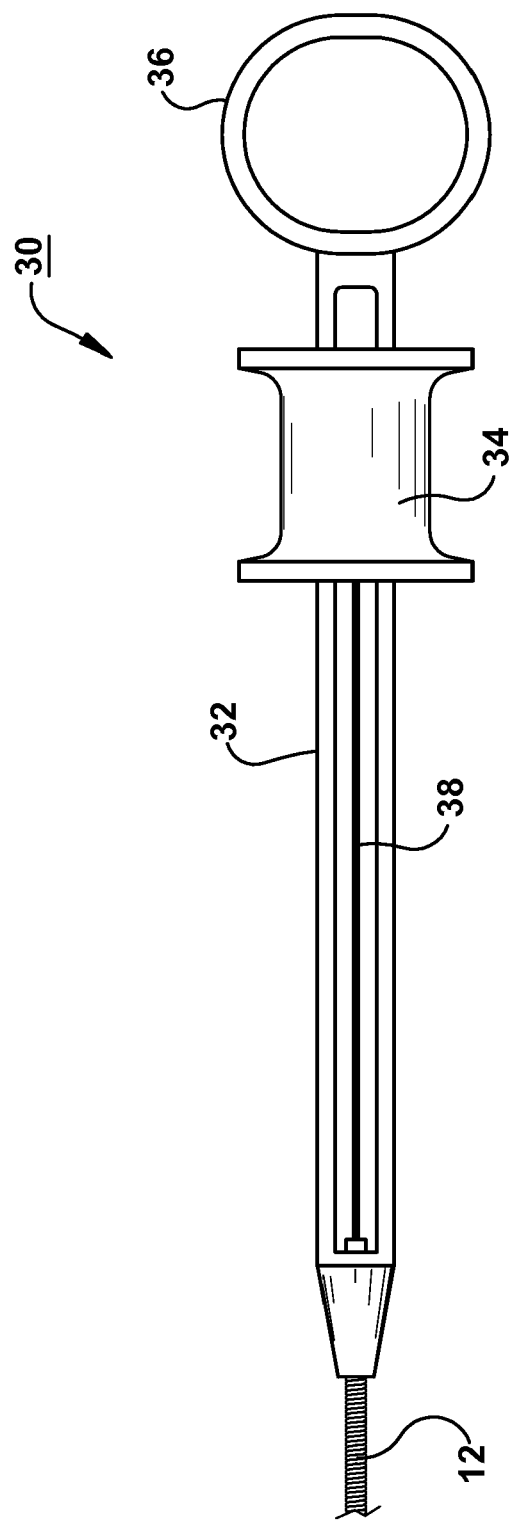
FIG. 9 is a front view of the proximal end of the endoscopic suture cutter of FIG. 1, showing a handle assembly.

Referring now to FIG. 9, a front view of the proximal end of the endoscopic suture cutter 10 is shown. A handle assembly 30 is shown and includes a base 32 and a slider 34.

The handle is used to transfer the linear motion of the slider to open and close the jaws on the distal end. In operation of the handle 30, a user may insert a thumb from one hand into a ring 36 and rest several fingers from the same hand on the slider 34. Movement of the slider 34 relative to the base 32 causes movement of a link 38. The link 38 may be attached directly or indirectly to the control wires 14, 16 within the spring sheath catheter 12. The user may open the cutting jaws by actuating the handle slider and moving it in the distal direction. The user may grasp a suture with a hook on the distal end of the cutting jaws and close the jaws by moving the slider in the proximal direction. The user may cut the suture by either closing the jaws completely, which cleaves the suture material, or by gently placing traction on the spring catheter sheath to slice the suture material. It should be apparent to one skilled in the art that the design and operation of the handle assembly and the link to the control wires may vary in the practice of this invention.

Referring again to FIG. 1, the spring sheath catheter 12 runs the length of the cutter 10 from the fork 18 to the handle 30. The spring sheath catheter 12 is formed of a coil wire and can be a variety of shapes, such as for example, a circular cross section or a rectangular cross section. The spring sheath may be PTFE (Teflon) coated or a heat shrink coated on the outside. The diameter of the spring sheath catheter 12 may vary in diameter, such as for example, the outside diameter range may be 0.080 to 0.100 cm. The length of the sheath is long enough to allow reasonable length beyond the proximal end and beyond the distal end of an endoscope, such as for example, the total length of the cutter 10 may be 165 cm.

Within the sheath, the two control wires run the length of the device. The control wires 14, 16 within the sheath 12 may be stainless steel, or any suitable material. The inside of the sheath may be coated with HDPE tubing running through the length of the device. The tubing reduces metal-on-metal contact between the sheath and the wires to reduce wear and provide for a smoother operation. Other friction-reducing structure may be used in the practice of this invention.

The fork provides a mounting location for the jaws. As shown in FIG. 1, the fork 18 includes two tangs 40, 42 protruding distally from a base 46. Each tang defines a mounting aperture through which the rivet 24 is placed. A space between the tangs allow for pivoting movement of the jaws 20, 22 in either rotational direction. Discussed herein in greater detail, each fork defines a recess 50 which is cooperatively shaped to allow insertion of a bump on a jaw.

Figure 2:
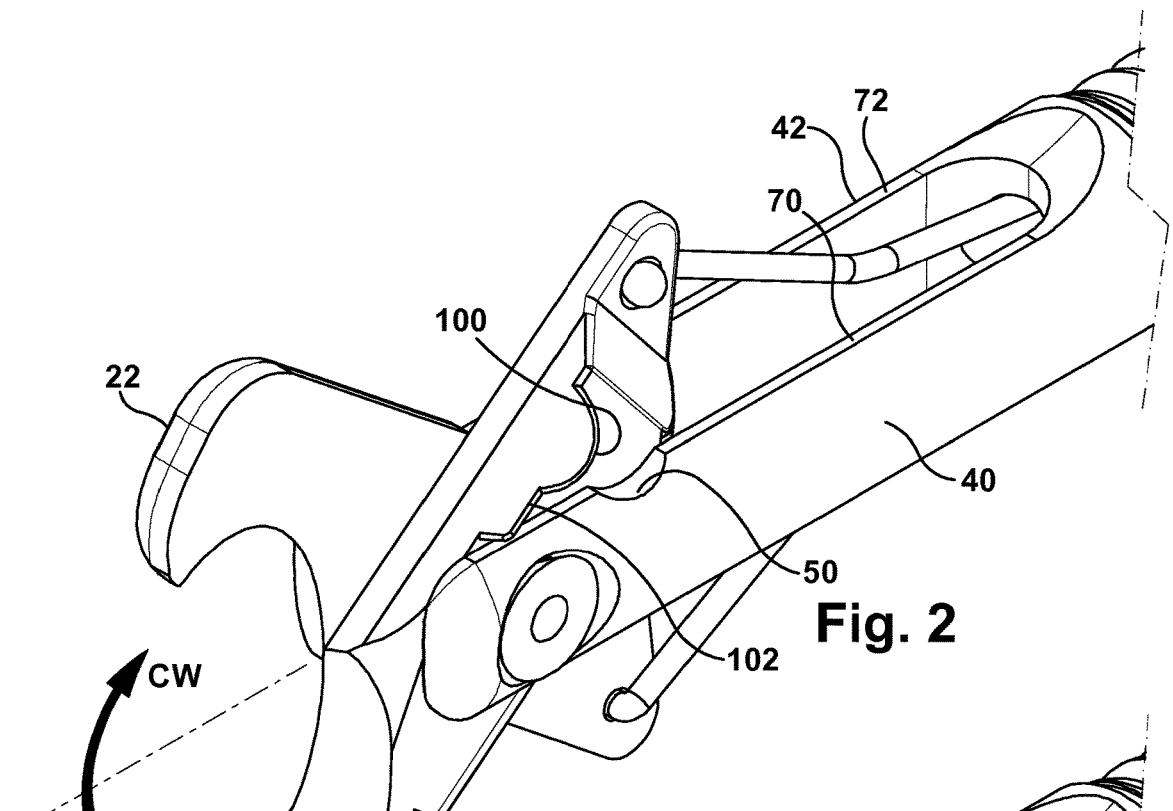
FIG. 2 is a front perspective view of the distal end of the endoscopic suture cutter of FIG. 1, with the jaws of the cutter shown in an open position.

A front perspective view of the distal end of the endoscopic suture cutter 10 is shown in FIG. 2. In this Figure, the jaws 20, 22 are shown in an open position. A similar open position is shown in the front view of FIG. 4. Specifically, the jaws 20, 22 are shown in a desired open position. The embodiment illustrated prohibits opening of the jaws beyond this position. For example, the jaws 20, 22 are rotated about 45 degrees away from the longitudinal axis Li of the fork. This embodiment is shown for exemplary purposes only, and the cutter 10 may be modified in the practice of the invention to allow the maximum opened condition to be more or less than 45 degrees.

As shown in FIG. 2, a bump 102 on the outside surface 104 of the first jaw 20 contacts the top ledge 70 of the first tang 40. This contact prohibits additional rotation of the distal end of the first jaw 20 in the counterclockwise CCW direction.

The second jaw 22 may be identical in shape and size as the first jaw 20. If so, although not shown, a bump on the outside surface of the second jaw 22 contacts the top ledge 72 of the second tang 42 in the illustrated open position. This contact prohibits additional rotation in the clockwise CW direction of the distal end of the second jaw 22.

Figure 3:
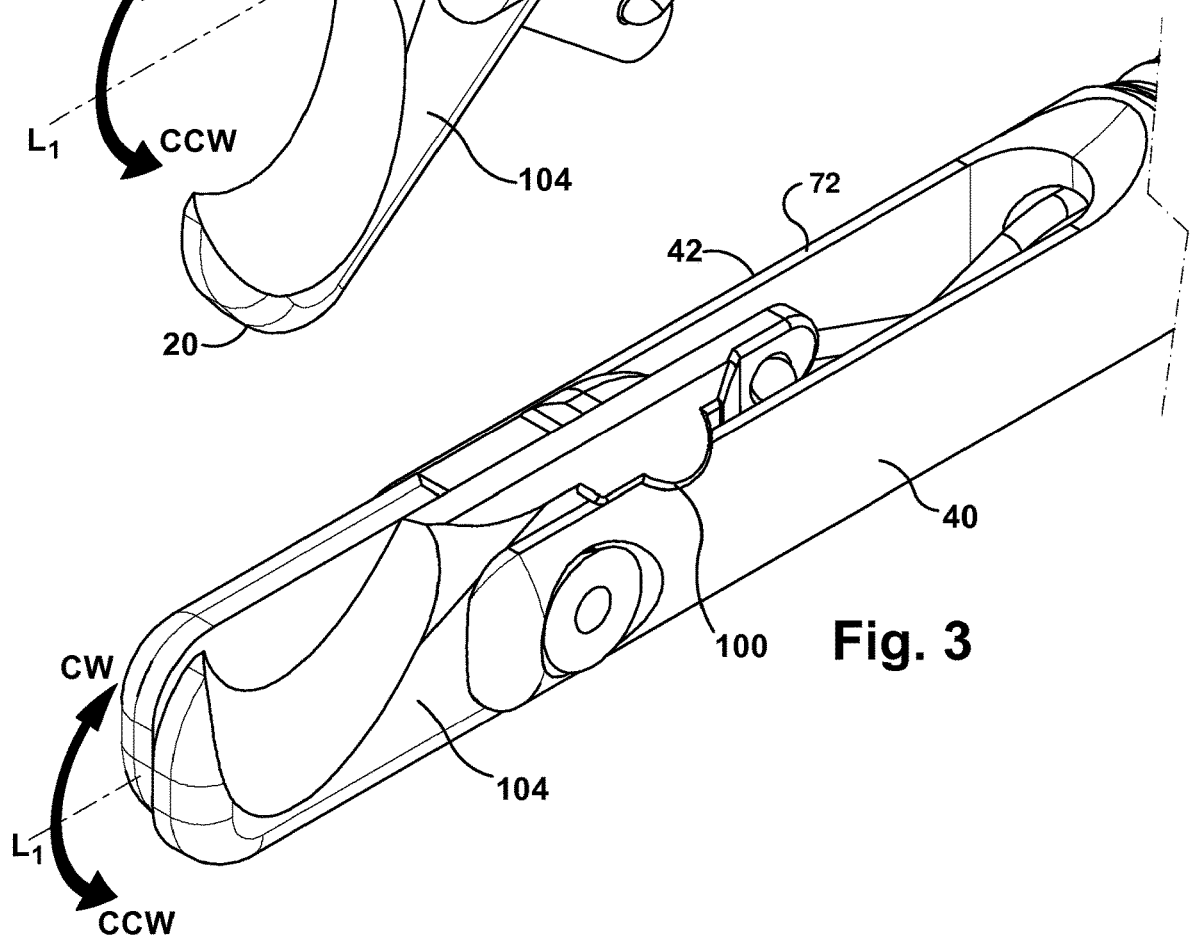
FIG. 3 is a front perspective view of the distal end of the endoscopic suture cutter of FIG. 1, with the jaws of the cutter shown in a closed position.

A front perspective view of the distal end of the endoscopic suture cutter 10 is shown in FIG. 3. In this Figure, the jaws 20, 22 are shown in a closed position. A similar closed view is shown in a front view in FIG. 5. The jaws are mounted to allow for an overlap in this closed position, such as for example, an overlap of 0.5 mm.

Specifically, the jaws 20, 22 are shown in a desired closed position. The embodiment illustrated prohibits closing of the jaws beyond this position. For example, the jaws 20, 22 are rotated to about a parallel position relative to the longitudinal axis Li of the fork. This embodiment is shown for exemplary purposes only, and the cutter 10 may be modified in the practice of the invention to allow the maximum closed condition to be more or less than 0 degrees relative to the longitudinal axis Li of the fork. However, the jaws 20, 22 will remain unstuck in the desired closed position and allow for retraction of the cutter 10 through the endoscope.

As shown in FIG. 3, a bump 100 on the outside surface 104 of the first jaw 20 contacts the recess 50 on the first tang 40. This contact prohibits additional rotation in the counterclockwise CW direction of the distal end of the first jaw 20.

The second jaw 22 may be identical in shape and size as the first jaw 20. If so, although not shown, a bump on the outside surface of the second jaw 22 contacts a recess in the top ledge 72 of the second tang 42. This contact prohibits additional rotation in the clockwise CCW direction of the distal end of the second jaw 22.

Figure 6:
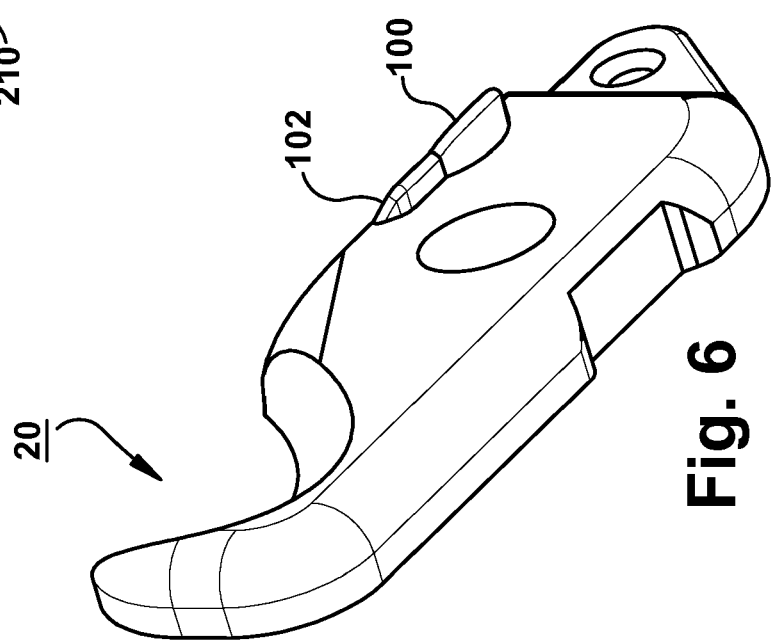
FIG. 6 is a front perspective view of a single jaw of the endoscopic suture cutter of FIG. 1.

As discussed herein, the first jaw and the second jaw may be identical in shape and size. For discussion purposes, the first jaw 20 is shown in various views in FIGS. 6-8. The first jaw 20 has several advantageous features. The distal end 200 of the jaw 20 is configured in a convex, parrot-like shape. All surfaces of the distal end 200 are rounded. With these rounded surfaces, a user is less likely to inadvertently scrape, cut or otherwise damage any gastrointestinal wall tissue during the suture cutting and removal procedure. Further, the overall shape of the concave, top surface 202 allows for the jaw 20 to be used by the user to snag imbedded sutures. The shape of the distal end illustrated is for exemplary purposes and may vary in other embodiments of the invention.

As discussed herein, the first jaw includes a bump 100. The bump as shown defines a curved surface extending away from the body of the jaw. In the embodiment shown, the bump has a height of 0.015 in. The height and shape of the bump may vary in the practice of the invention. As discussed, the recess 50 on the fork is correspondingly shaped to receive the bump during opening and closing of the jaws. The first jaw also defines an aperture 204 for insertion of the rivet and a bottom recess 206.

Figure 7:
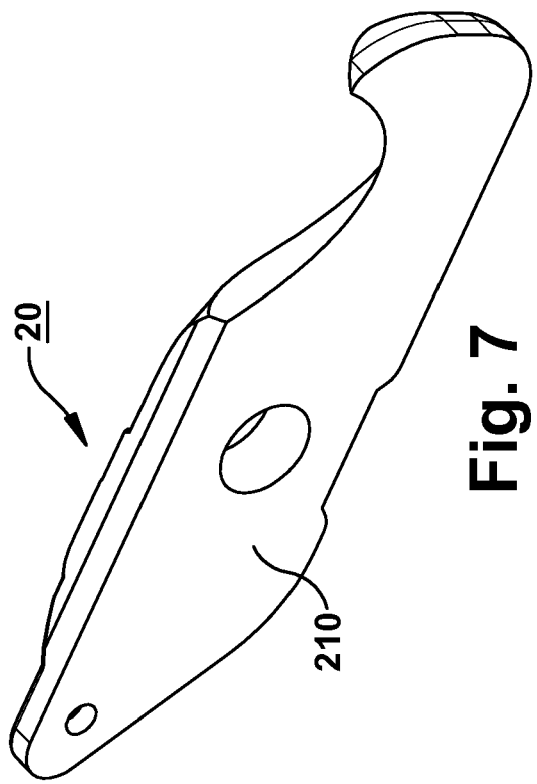
FIG. 7 is a rear perspective view of the jaw of FIG. 6.
Figure 8:
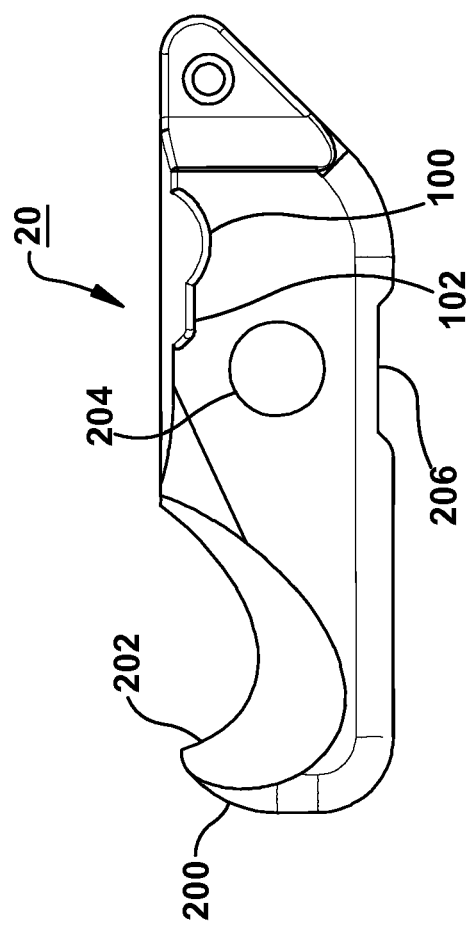
FIG. 8 is a front view of the jaw of FIG. 6.

The sharpness of the jaws is an important feature in the performance of the cutter. Jaws are sharpened as manufactured to either cut or rip, that is to say, slice, the suture. Jaws can also be used to grasp suture for removal. As shown in FIG. 7, the inside surface 210 of first jaw 20 is planar, smooth and without any raised portions, bumps, or stoppers. This configuration allows for more automated sharpening, and at a lower cost to the manufacturer. The jaws are very small and create difficulty in bracing before any sharpening process begins which involves any significant force. By having a smooth inside surface, and all contours on an outside surface, the jaw shape allows for a sharpening of a plurality of jaws at the same time, and at a relatively inexpensive cost. For example, with the contours of the jaws held in a mold-like brace, for example, in a downward orientation, and the smooth inside surface exposed in an upward orientation, a plurality of jaws may be sharpened efficiently by a high-volume sharpening apparatus, such as a wheel sharpener.

A method of operation of the endoscopic suture cutter as described herein is also inherent to the present invention.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A cutting device for use with an endoscope, the device comprising:
   a base;
   a first tang and a second tang protruding distally from the base;
   a first jaw and a second jaw pivotally mounted on the first tang and the second tang, and movable between a predetermined closed position and a predetermined open position;
   wherein the first jaw comprises a bump,
   wherein the first tang defines a recess cooperatively shaped to receive the bump, and
   wherein the bump is received in the recess at the predetermined closed position to prohibit the first jaw from moving into an over-closed position.

2. The cutting device of claim 1, wherein the first jaw and second jaw each comprises at least one contoured surface section and at least one planar surface section, wherein the first and second jaws are positioned to have the planar surfaces face each other.

3. The cutting device of claim 1, wherein the first jaw comprises a convex outer surface at a distal end having a smooth surface section, and a sharpened edge having a concave shape at the distal end.

4. The cutting device of claim 1, wherein the first jaw and the second jaw are pivotally mounted in between the first tang and the second tang.

5. The cutting device of claim 1, wherein the bump is disposed on an outward facing surface of the first jaw.

6. The cutting device of claim 1, wherein at least one of the first jaw and the second jaw comprises a protrusion, wherein the protrusion contacts at least one of the first tang and the second tang at the predetermined open position to prohibit movement of at least one of the first jaw and the second jaw in an opening direction.

7. The cutting device of claim 6, wherein the protrusion is disposed on an outward facing surface of at least one of the first jaw and the second jaw.

8. The cutting device of claim 1, wherein the first jaw and the second jaw are identical.

9. The cutting device of claim 8, wherein the first tang and the second tang are identical.

10. A method of cutting an object with an endoscopic tool, comprising the steps of:
    inserting an endoscopic tool having an end effector into a cavity, the end effector comprising a first jaw and a second jaw;
    moving the end effector from a predetermined closed position to a predetermined open position;
    maneuvering the end effector to snag a targeted object; and
    moving the end effector from the predetermined open position to the predetermined closed position, such that the first jaw and the second jaw cut the targeted object,
    wherein the first jaw and the second jaw are pivotally mounted on a first tang and a second tang of the end effector,
    wherein the first jaw comprises a bump,
    wherein the first tang defines a recess cooperatively shaped to receive the bump, and
    wherein the bump is received in the recess at the predetermined closed position to prohibit the first jaw from moving into an over-closed position.

11. The method of claim 10, wherein the targeted object is a suture.

12. The method of claim 10, wherein at least one of the first jaw and the second jaw comprises a protrusion, wherein the protrusion contacts at least one of the first tang and the second tang at the predetermined open position to prohibit movement of at least one of the first jaw and the second jaw in an opening direction.

13. The method of claim 12 further comprising the step of stopping the first jaw and the second jaw from opening farther than the predetermined open position by having the protrusion contact at least one of the first tang and the second tang when the end effector reaches the predetermined open position.

14. The method of claim 10 further comprising the step of stopping the first jaw and the second jaw from closing farther than the predetermined closed position by having the bump received in the recess defined by the first jaw when the end effector reaches the predetermined closed position.

15. A cutting device for use with an endoscope, the device comprising:

a fork; and two jaws pivotally mounted to the fork, and movable between a predetermined closed position and a predetermined open position;

wherein the fork comprises a first tang and a second tang, and the two jaws are pivotally mounted in between the first tang and the second tang, wherein at least one of the two jaws have at least one bump on an outward facing surface of the jaw, and the at least one bump prohibits movement of the two jaws in a closing direction beyond the predetermined closed position, and wherein the at least one bump defines a curved surface extending away from the outward facing surface of the jaw, wherein the outward facing surface is a surface not facing the other jaw, and wherein the at least one bump contacts at least one of the first tang and the second tang at the predetermined closed position to prohibit at least one of the two jaws from closing farther than the predetermined closed position.

16. The cutting device of claim 15, wherein at least one of the two jaws have a protrusion that contacts at least one of the first tang and the second tang to prohibit movement of the two jaws in an opening direction beyond the predetermined open position.

17. The cutting device of claim 15, wherein the two jaws are identical.

\* \* \* \* \*